United States Patent
Divi et al.

(10) Patent No.: US 10,781,170 B1
(45) Date of Patent: Sep. 22, 2020

(54) PROCESS FOR PREPARING BRIVARACETAM

(71) Applicant: Divi's Laboratories Ltd., Hyderabad (IN)

(72) Inventors: Murali Krishna Prasad Divi, Hyderabad (IN); Mysore Aswatha Narayana Rao, Hyderabad (IN); Shaik Nowshuddin, Hyderabad (IN)

(73) Assignee: Divi's Laboratories Ltd. (IN)

( * ) Notice: Subject to any disclaimer, the term of this patent is extended or adjusted under 35 U.S.C. 154(b) by 0 days.

(21) Appl. No.: 16/661,349

(22) Filed: Oct. 23, 2019

(30) Foreign Application Priority Data

Oct. 21, 2019 (IN) .............................. 201941042636

(51) Int. Cl.
*C07D 207/12* (2006.01)
(52) U.S. Cl.
CPC ........ *C07D 207/12* (2013.01); *C07B 2200/07* (2013.01)
(58) Field of Classification Search
CPC .......................... C07D 207/12; C07B 2200/07
USPC ....................................................... 514/424
See application file for complete search history.

(56) References Cited

U.S. PATENT DOCUMENTS

| 8,338,621 B2 | 12/2012 | Surtees et al. |
| 8,957,225 B2 | 2/2015 | Carroll |

FOREIGN PATENT DOCUMENTS

| WO | 0162726 A2 | 8/2001 |
| WO | 0162726 A3 | 8/2001 |
| WO | 2011077463 A1 | 6/2011 |
| WO | 2016075082 A1 | 5/2016 |

OTHER PUBLICATIONS

European Search Report dated Mar. 30, 2020.
Mansoori, et al., Development of a new synthesis approach for S-pregabalin by optimizing the preparation stages, Journal of the Iranian Chemical Society (2020) 17:89-101.
Alexander N. Reznikow, et al, Nitroalkenes in the Ni(II) Catalyzed Asymmetric Michael Addition, Convenient Route to the Key Intermediate of Brivaracetam, Helvetica Chimica Acta/ vol. 101, Oct. 2018 (Abstract).

*Primary Examiner* — Kristin A Vajda
(74) *Attorney, Agent, or Firm* — Caesar Rivise, PC

(57) ABSTRACT

A process for the preparation of Brivaracetam, an anti-convulsion drug, is provided comprising Hofmann rearrangement of (S)-3-(2-(chloroamino)-2-oxoethyl) hexanoic acid, followed by cyclization resulting in (R)-4-propyl-pyrrolidin-2-one which on condensation with bromo butyric acid or ester followed by reaction with ammonia results in Brivaracetam.

4 Claims, No Drawings

PROCESS FOR PREPARING BRIVARACETAM

This application claims benefit of IN Application No. 2019/41042636, filed Oct. 21, 2019, the contents of which are incorporated in their entirety herein.

FIELD OF INVENTION

The present invention relates to an improved process for the preparation of Brivaracetam, a drug useful in treating epilepsy and related central nervous system disorders.

BACKGROUND OF THE INVENTION

Brivaracetam is chemically (2S)-2-[(4R)-2-oxo-4-propyl-pyrrolidin-1-yl] butanamide, having the structure:

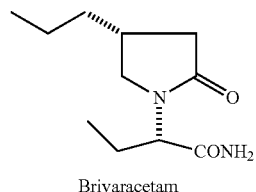

Brivaracetam

Brivaracetam and a process for its preparation were first disclosed in WO 01/62726 (Scheme 1). The 5-hydroxy-4-propyl-furan-2-one is condensed with S-2-aminobutyramide through reductive amination followed by further reduction to give racemic Brivaracetam.

The racemic Brivaracetam is resolved using chiral chromatography.

The U.S. Pat. No. 8,957,226 B2 describes the synthesis of Brivaracetam where hex-2-enoic acid ethyl ester is reacted with nitromethane followed by reduction resulting in racemic lactam (Scheme 2). It is resolved using chiral chromatography to obtain (R)-4-propyl-pyrrolidin-2-one which on condensation with racemic methyl ester of 2-bromobutyric acid followed by the reaction with ammonia results in racemic Brivaracetam. A second chiral chromatography for the resolution of the racemic mixture results in Brivaracetam.

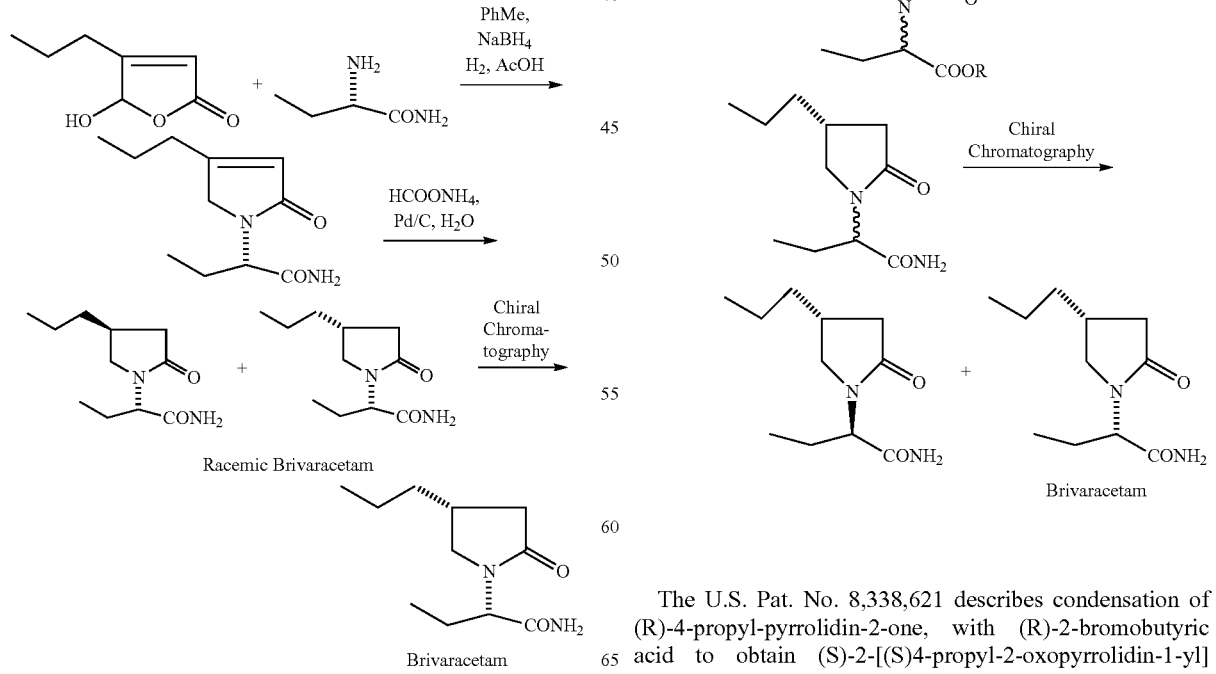

The U.S. Pat. No. 8,338,621 describes condensation of (R)-4-propyl-pyrrolidin-2-one, with (R)-2-bromobutyric acid to obtain (S)-2-[(S)4-propyl-2-oxopyrrolidin-1-yl] butyric Acid (Scheme 3) which can be converted into Brivaracetam.

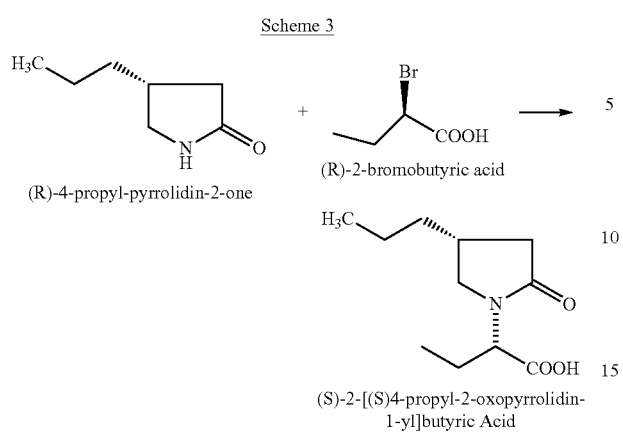

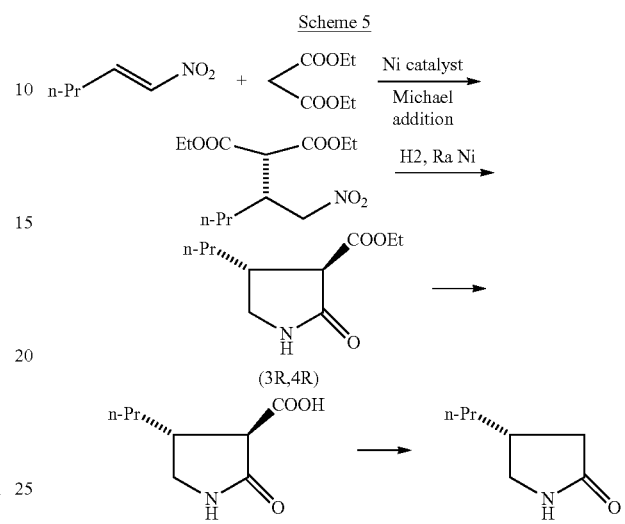

Thus, (R)-4-propyl-pyrrolidin-2-one is a key intermediate for the preparation of Brivaracetam.

The process for the preparation of (R)-4-propyl-pyrrolidin-2-one is described in WO 2016075082 A1 (Scheme 4). It involves selective amination of racemic aldehyde using the enzyme LIT-transaminase to obtain (R)-amine followed by cyclization. The enzyme has been obtained from several microorganisms out of which enzyme from *Hyphomonas neptunium* exhibited highest selectivity with 92% ee.

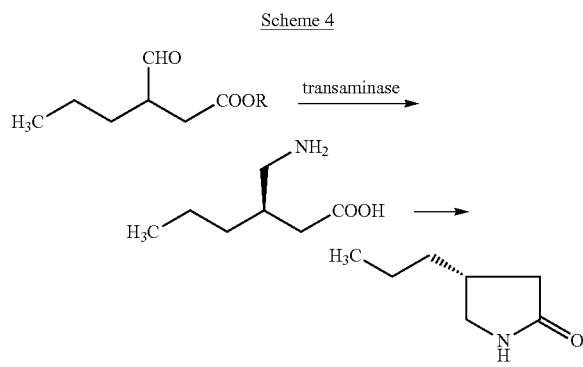

Reznikov et al (*Helvetica Chimica Acta*, 2018, 101, e1800170) reported a chiral synthesis of (R)-4-propyl-pyrrolidin-2-one by applying asymmetric Michael addition using Nickel catalysts. Reaction of 1-nitropent-1-ene with diethylmalonate in the presence of Ni (II) complex with chiral ligand (1R,2R)-1,2-diphenylethane-1,2-diamine catalyst results in chiral nitro malonate derivative which on hydrogenation results predominantly in (3R,4R) isomer ester. Base catalyzed hydrolysis of the ester followed by decarboxylation by refluxing in toluene results in (R)-4-propyl-pyrrolidin-2-one (Scheme 5).

Thus, all prior art processes for the preparation of the key intermediate, (R)-4-propyl-pyrrolidin-2-one are complicated making the overall process for Brivaracetam expensive. There is a need for developing a simple and cost-effective process for (R)-4-propyl-pyrrolidin-2-one.

SUMMARY OF THE INVENTION

The objective of the present invention is to develop a novel process for the key intermediate, (R)-4-propyl-pyrrolidin-2-one (I) which can be converted into Brivaracetam. The process comprises (Scheme 6), the chlorination of (S)-3-(2-amino-2-oxoethyl) hexanoic acid (II) to obtain the (S)-3-(2-(chloroamino)-2-oxoethyl) hexanoic acid (III). The compound (III) after Hofmann rearrangement followed by cyclization in one pot reaction gives the required (R)-4-propyl-pyrrolidin-2-one (I) in high yields (85%) and purity. The Hofmann rearrangement product, (R)-3-(aminomethyl) hexanoic acid (IV) can also be isolated in pure form and in good yields. However, surprisingly, cyclization of (IV) gives (I) in poor yields (32%). The intermediate (I) can be converted into Brivaracetam through prior art methods.

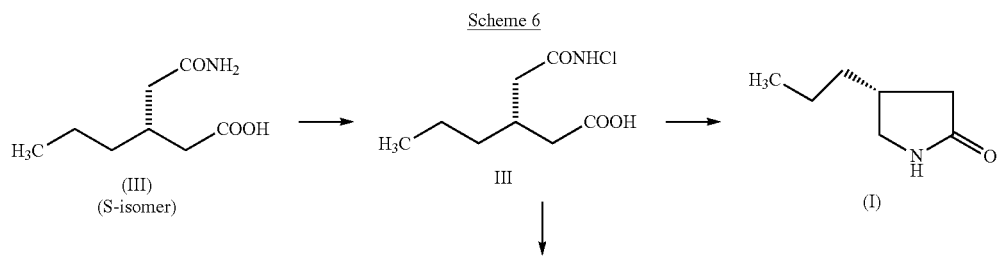

-continued

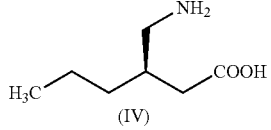
(IV)

The required starting compound (S)-3-(2-amino-2-oxoethyl) hexanoic acid (II) is prepared from 4-propyl piperidine-2, 6-dione (V), a known compound (Scheme 7). Hydrolysis of (V) results in racemic 3-(2-amino-2-oxoethyl) hexanoic acid (VI), which on resolution using (S)-(−)-1-Phenylethylamine gives pure (S)-enantiomer (II).

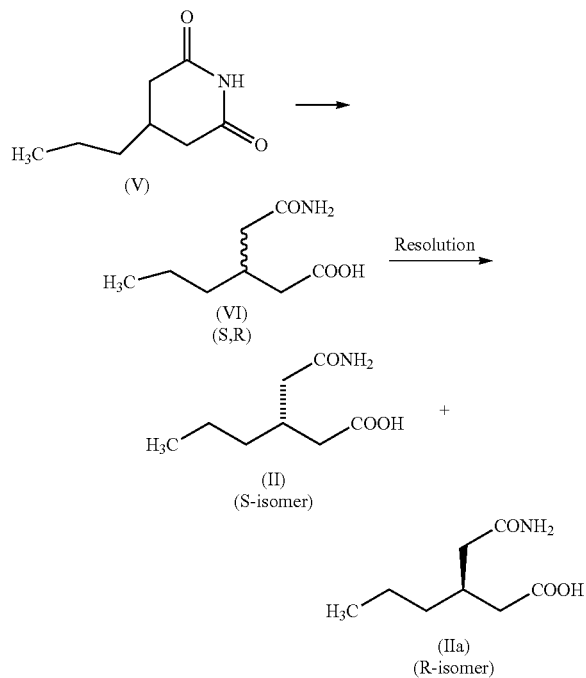

Another aspect of the present invention is the recovery of the unwanted (R)-isomer (IIa). Dehydration of (IIa) results in 4-propyl piperidine-2, 6-dione (V) (Scheme 8).

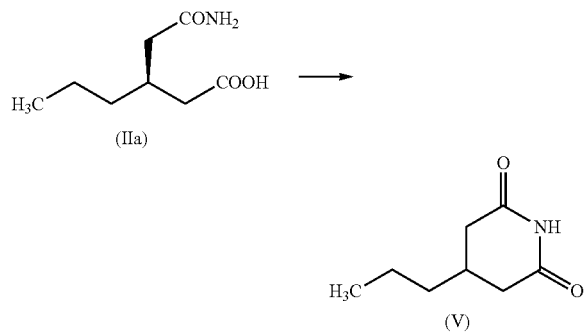

The (V) being a symmetrical molecule, has no chirality and can be recycled.

The present process for the preparation of (I) offers several advantages over prior art methods:
1. It avoids the use of hazardous and explosive nitromethane (scheme 2).
2. Prior art processes use chiral chromatography technique for separation of the isomers (Scheme 1 & 2) which is not suitable at industrial scale. The present process uses conventional resolution method making the process economical. Furthermore, resolution is carried out in this invention at the early stage which usually reduces wastage of advanced intermediate.
3. Expensive reagents such as nickel catalyst with chiral ligands or specialized microbial transaminase enzyme are avoided.
4. The unwanted (R)-isomer (11a) formed in the process is valorized by converting into a symmetrical molecule which can be recycled.

DETAILED DESCRIPTION OF THE INVENTION

The present invention provides a novel process for the preparation of Brivaracetam which comprises the steps of:
a) reacting (S)-3-(2-amino-2-oxoethyl) hexanoic acid (II) with a chlorinating agent to obtain (S)-3-(2-(chloroamino)-2-oxoethyl) hexanoic acid (III), and
b) subjecting the compound (III) to Hofmann rearrangement followed by thermal cyclization, in one pot, to obtain (R)-4-propyl-pyrrolidin-2-one (I), and
c) optionally, subjecting the compound (III) to Hofmann rearrangement to obtain (R)-3-(aminomethyl) hexanoic acid having the structure (IV), and cyclizing the compound (IV) to obtain (R)-4-propyl-pyrrolidin-2-one (I), and
d) converting the reaction product of step (b) or (c) into Brivaracetam.

The required starting compound (S)-3-(2-amino-2-oxoethyl) hexanoic acid (II) can be prepared from 4-propyl piperidine-2, 6-dione (V) as described in Scheme 7. The compound (V) itself, can be prepared by reacting 3-(carboxymethyl) hexanoic acid with urea as described in the prior art (*Australian Journal of Chemistry*, 1960, Volume 13, Number 1, p 129-144).

Hydrolysis of (V) in aqueous sodium hydroxide results in 3-(2-amino-2-oxoethyl) hexanoic acid (VI). Because of the generation of a chiral center, the compound (VI) is a racemic mixture. The hydrolysis reaction can be carried out conveniently using one equivalent sodium hydroxide at a temperature between 45° C. and 55° C. The reaction completes in about 30 to 60 mins. If the reaction is carried out at room temperature, it requires about 3 to 5 hours for the completion. At reflux temperature, the yield of (VI) is reduced because of the formation of dicarboxylic acid, 3-(carboxymethyl)hexanoic acid, as a side product. Dicarboxylic acid formation is also observed when acid is used for the hydrolysis.

The racemic mixture of (VI) can be resolved using chiral bases. The treatment of (VI) with (S)-(−)-1-phenylethylamine in chloroform results in the selective precipitation of (S)-3-(2-amino-2-oxoethyl) hexanoic acid (II) as a salt of (S)-(−)-1-Phenylethylamine. Hydrolysis of the salt, using acid, results in (S)-3-(2-amino-2-oxoethyl) hexanoic acid (II) having chiral purity of about 92%. The chiral purity can be further improved by making a salt of dicyclohexylamine in acetone, followed by its breaking the salt using dilute sulfuric acid. This results in the compound (II) with 98.2% chiral purity.

Reacting (II) with a chlorinating agent, results in (S)-3-(2-(chloroamino)-2-oxoethyl) hexanoic acid (III) as a colorless crystalline compound. No loss in the chirality is observed during the N-chlorination. The chlorination can be carried out using several reagents such as trichloroisocyanuric acid, sodium dichloroisocyanurate, N-chlorosuccininmide, etc. Excellent yield and purity are obtained when trichloroisocyanuric acid is used as the chlorinating agent.

The reaction can be conveniently carried out by dissolving (II) in methanol and treating with about 0.3 equivalent trichloroisocyanuric acid at room temperature. The reaction is fast and completes in about 30 mins During the reaction cyanuric acid precipitates out and can be recovered by filtration and re-cycled. Removal of the solvent and slurrying the residue with hexane results in (III) in high yields (90%) having high chemical purity (>99.5%) and chiral purity (98%). The SciFinder search shows that the chiral crystalline compound (III) is not reported in the literature until date. When sodium dichloroisocyanurate is used as the chlorinating agent, (III) is obtained in lower yields (60%). Chlorination with N-chlorosuccinimide results in much lower yields. When sodium hypochlorite solution is used for chlorination, the reaction does not stop at N-chlorination but proceeds further to undergo Hofmann rearrangement resulting in the amino compound (IV). Acidification of the reaction mixture and extraction with n-butanol results in the amino compound (IV) in 82% yield having 96% chemical purity and 92% chiral purity.

The reaction of the N-chloro compound (III) with a base such as sodium hydroxide in water at room temperature results in Hofmann rearrangement. Acidification of the reaction mixture followed by extraction with n-butanol results in the amino compound (IV) in high yields (90%) with high chemical purity (>97%) and chiral purity (96%). Thus the yields and purity of the compound (IV) resulting from N-chloro compound, (III) is much higher than that obtained from the reaction using sodium hypochlorite.

Attempts to convert the amine (IV) to lactam (I) by heating at a temperature of about 90° C. in toluene for about 36 hours, results in 32% yield of (I). Its chemical purity is about 98.3% and chiral purity about 98.1%.

However, when the chloro compound, (III) was first treated with aqueous sodium hydroxide at room temperature for about 12 hours, followed by addition of toluene and heating the biphasic reaction mixture at a temperature of about 90° C. for about 36 hours and after usual workup produced (I) in 85% yield with high chemical (98.5%) and chiral (98.9%) purity. Thus, one pot conversion of (III) to (I) without isolating the intermediate amino compound (IV) results in high yields and purity. Although the exact reason for obtaining higher yields are not clear, we believe there is a possibility that when the chloro compound (III) is converted to lactam (I), formation of hydrochloric acid may partially neutralize the alkalinity of the medium facilitating better conversion to lactam. Such a situation is not possible with a non-chloro compound.

Whatever may be the reason, lactam (I) is obtained in high yields and purity from chloro compound (III) which is a novel compound described in this invention.

Carrying out Hofmann rearrangement using chlorinating agent such as trichloroisocyanuric acid has several advantages over the generally used sodium hypochlorite. Sodium hypochlorite is used as a solution and is unstable and hazardous. In comparison, trichloroisocyanuric acid is a solid which can be handled easily. It is also inexpensive and because of the three chloro atoms present, only 0.3 mole equivalent is needed for one mole of the substrate. The byproduct formed during the reaction, cyanuric acid, is also a solid and can be recycled.

The chirally pure (R)-4-propyl-pyrrolidin-2-one (I) can be reacted with (R)-2-bromobutyric acid or ester followed by reaction with ammonia to obtain brivaracetam as described in the prior art. During the resolution step of (VI), after obtaining the (S)-isomer (II), the unwanted (R)-isomer (IIa) remains in the filtrate. The (IIa) can be easily converted to (V) and can be reused (Scheme 8). Enantiomerically enriched (IIa) can be azeotropically dehydrated by heating in toluene in the presence of boron trioxide or p-toluenesulfonic acid in catalytic amount resulting in (V). The chirality of the (IIa) gets eliminated when it is converted to (V) a symmetrical molecule.

The embodiments of the present invention are further described in the following examples, which are not intended in any way to limit the scope of the invention.

EXAMPLES

Example 1: Preparation of 4-propylpiperidine-2,6-dione (V)

A suspension of n-butyraldehyde (25 gm, 0.35 mol), 2-cyanoacetamide (58.5 gm, 0.70 mol), and potassium hydroxide (0.75 gm, 0.013 mol) in water (175 mL) was stirred at 25° C. to 30° C. for 5 to 6 hours. To the reaction mixture was added 216 mL of 36% HCl and heated to 95° C. to 100° C. to get a clear solution. The solution was stirred at this temperature for 12 to 15 hours. After completion of the reaction (monitored by TLC), the reaction mixture was extracted with 3×100 mL methyl tert-butyl ether. The organic layers were pooled, dried over anhydrous sodium sulfate, and concentrated to obtain a crude residue of 3-propylpentanedioic acid. To the crude residue was added urea (25 gm, 0.42 mol) and heated to 140 to 150° C. The reaction mass was stirred at this temperature for 4 to 5 hours. The reaction mixture was cooled to 90° C. and 200 mL water was added. The reaction mixture was further cooled to 5 to 10° C. and stirred for about 30 mins. The precipitated product was filtered, washed with 50 mL cold water and dried to yield 4-propylpiperidine-2,6-dione (V). Yield: 33.6 gm (62.4%), Purity by HPLC: 99.3%.

Example 2: Preparation of (RS)-3-(2-amino-2-oxoethyl) hexanoic acid (VI)

Sodium hydroxide (10.5 gm, 0.26 mol) was added to a suspension of 4-propylpiperidine-2,6-dione (V) (34.0 gm, 0.22 mol) in water (150 mL) at 25° C. to 30° C., and stirred for 10 mins to get a clear solution. The solution was heated to 50° C. to 55° C. and stirred for 30 mins. After completion of the reaction (monitored by TLC), the reaction mixture was cooled to 0° C. to 5° C. and pH adjusted to 1.0 with 36% HCl. After stirring for 30 mins, the precipitated product was filtered, washed with 100 mL of cold water and dried to yield (RS)-3-(2-amino-2-oxoethyl) hexanoic acid (VI). Yield: 35.3 gm (93%), M.R: 128-130° C., Purity by HPLC: 99.5%.

Example 3: Preparation of (S)-3-(2-amino-2-oxoethyl) hexanoic acid (II)

(RS)-3-(2-amino-2-oxoethyl) hexanoic acid (VI) (50.0 gm, 0.28 mol) was dissolved in a mixture of 500 mL chloroform and 18 mL ethanol. The solution was heated to 50° C. Portionwise, S-(−)-1-Phenylethylamine (35.0 gm, 0.28 mol) was added and the reaction mass was stirred for 30 mins at 50° C. The reaction mass was cooled to room temperature and stirred overnight.

The precipitated salt was filtered. The filtrate was kept aside for recovering the unwanted R-isomer (IV). The precipitated salt was added to 100 mL water and pH adjusted to about 13.0 using 40% solution of sodium hydroxide. The reaction mass was extracted with 3×50 mL chloroform from which S-(−)-1-Phenyl ethyl amine was recovered. The aqueous layer was cooled to 0-5° C. and its pH was adjusted to 2.0 using 36% HCl. After stirring for 20 mins, the precipitated solid was collected to obtain (S)-3-(2-amino-2-oxoethyl) hexanoic acid (II). Yield: 22.5 gm (40%), Purity by HPLC: 99.2%, chiral purity: 92.5%.

The chiral purity can be further improved by preparing the salt of dicyclohexylamine. To the solution of acid (II) (5.0 gm, 0.0288 mole, chiral purity: 92.5%) in 30 mL acetone was added dicyclohexylamine (5.23 gm, 0.0288 mole) at room temperature and stirred for 2 hours. The precipitated salt was collected by filtration. The salt was suspended in water and the pH was adjusted to 2.0 using 20% solution of sulfuric acid at 0-5° C. and stirred for 20 mins. The solid was filtered washed with water and dried under vacuum. Yield: 4.77 gm (95.5%), Purity by HPLC: 99.4%, chiral purity: 98.2%.

Example 4: Preparation of (S)-3-(2-(chloroamino)-2-oxoethyl) hexanoic acid (III) Using trichloroisocyanuric acid (S)-3-(2-amino-2-oxoethyl) hexanoic acid (II) (10.0 gm, 0.057 mol) was dissolved in 60 mL methanol and was added 5.36 gm (0.023 mol) trichloroisocyanuric acid portion wise. The solution was stirred for 30 mins; precipitated cyanuric acid was removed by filtration. The filtrate was concentrated under reduced pressure. The residue was slurried with 25 mL hexane and filtered to obtain (S)-3-(2-(chloroamino)-2-oxoethyl) hexanoic acid (III) as white solid. Yield: 10.8 gm (90%), Purity by HPLC: 99.8%, chiral purity: 98.8%, Melting Range: 85-86.5° C.

Example 5: Preparation of (S)-3-(2-(chloroamino)-2-oxoethyl) hexanoic acid (III) Using sodium dichloroisocyanurate (S)-3-(2-amino-2-oxoethyl) hexanoic acid (II), 5.0 gm (0.028 mol), was dissolved in 30 mL methanol and was added sodium dichloroisocyanurate (2.54 gm, 0.0115 mol) portionwise. The solution was stirred for 2 hours; precipitated cyanuric acid derivative was removed by filtration. The filtrate was concentrated under reduced pressure. The residue obtained was slurried with 25 mL hexane and filtered to obtain (R)-3-(2-(chloroamino)-2-oxoethyl) hexanoic acid (III) as white solid. Yield: 3.6 gm (61%), Purity by HPLC: 98.7%, chiral purity: 98.3%.

Example 6: Preparation of (R)-3-(aminomethyl) hexanoic acid (IV)

To a cooled (0-5° C.) solution of 12.0 gm sodium hydroxide in 100 mL water was added 10.0 gm (0.048 mol) of (III) portion wise. The reaction mixture was allowed to reach room temperature and stirred for 3 hours. The pH of the solution was adjusted to 2.0 using 36% HCl and extracted with 50 mL n-butanol. The organic layer was concentrated to obtain (R)-3-(aminomethyl) hexanoic acid (IV) as oil. Yield: 6.7 gm (90%). Purity by HPLC: 98.3%, Chiral purity: 98.5%

Example 7: Preparation of (R)-4-propyl-pyrrolidin-2-one (I) from (IV)

The compound (IV) (5.0 gm, 0.034 mol) was dissolved in 50 mL water. Toluene (100 mL) and sodium hydroxide (6.8 gm) were added to the reaction mixture. The reaction mixture was heated to a temperature of 85 to 95° C. for 36 hours. The toluene layer was separated and concentrated to remove the solvent completely under reduced pressure to get (R)-4-propyl-pyrrolidin-2-one (I) as oil. Yield: 1.4 gm (32%). Purity by GC: 98.3%, Chiral purity: 98.1%.

Example 8. Preparation of (R)-4-propyl-pyrrolidin-2-one (I) from (III)

(R)-3-(2-(chloroamino)-2-oxoethyl) hexanoic acid (III) (10.0 gm, 0.048 mol) was added portion wise to a cooled (0-5° C.) solution of 100 mL sodium hydroxide (12.0 gm) and stirred for 3 hours and again at 15-20° C. for 12 hours. The reaction mixture was heated to 90° C. and was added to 50 mL toluene and stirred for 36 hours at 90° C. The toluene layer was separated and concentrated to remove the solvent completely under reduced pressure to obtain (R)-4-propyl-pyrrolidin-2-one (I) as oil. Yield: 5.2 gm (85%), Purity by GC: 99.3%, Chiral purity: 99.1%.

Example 9: Preparation of (R)-3-(aminomethyl) hexanoic acid (IV) from (S)-3-(2-amino-2-oxoethyl) hexanoic acid (II) Using sodium hypochlorite To a solution of sodium hydroxide (2.0 gm, 0.51 mol in 10 mL water) was added the compound (II) (3.0 gm, 0.0173 mol) and cooled to 0-5° C. To the reaction mixture was added 20 mL of 14% sodium hypochlorite solution and stirred for 1 hour. The reaction mixture was allowed to come to room temperature and stirred for three more hours till the completion of the reaction (monitored by TLC). About 0.3 gm sodium bisulfite was added to neutralize the excess sodium hypochlorite. After cooling the reaction mixture to 0-5° C., the pH was adjusted to 2.0 using 36% HCl solution and was extracted with 3×25 mL n-butanol. The organic layer was concentrated, and the solvent was removed completely to obtain (R)-3-(aminomethyl) hexanoic acid (IV) as an oil. Yield: 2.06 gm (82%) Purity by HPLC: 98.3%, Chiral purity: 98.7%.

Example 10: Preparation of (R)-4-propyl-pyrrolidin-2-one (I) from (II) Using sodium hypochlorite To a solution of sodium hydroxide (2.0 gm, 0.51 mol in 10 mL water) was added the compound (II) (3.0 gm, 0.0173 mol) and cooled to 0-5° C. To the reaction mixture was added 20 mL of 14% sodium hypochlorite solution and stirred for 1 hour. The reaction mixture was allowed to come to room temperature and stirred for three more hours till the completion of the reaction (monitored by TLC). About 0.3 gm sodium bisulfite was added to neutralize the excess sodium hypochlorite. The pH was adjusted to 14.0 using 50% solution of sodium hydroxide and 30 mL toluene was added. The reaction mixture was refluxed for 36 hours. The two layers were separated. The toluene layer was washed with water and concentrated, and the solvent was removed completely to obtain (R)-4-propyl-pyrrolidin-2-one (I) as oil. Yield: 0.72 gm (32%), Purity by GC: 98.1%, Chiral purity: 98.3%.

Example-11: Preparation of 4-propylpiperidine-2,6-dione (V) from Unwanted isomer (R)-3-(2-amino-2-oxoethyl) hexanoic acid (IIa) Using boron trioxide A mixture of Enantiomeric enriched (R)-3-(2-amino-2-oxoethyl) hexanoic acid (IIa) (5.0 gm, 0.029 mol) and boron trioxide (1.0 gm, 0.014 mol) were suspended in toluene (50 mL) and stirred at 105° C. to 110° C. for 12 to 15 hours and liberated water was collected using Dean-Stark apparatus. The reaction mixture was cooled to 25° C. to 30° C. and filtered. The filtrate was washed with 5% NaHCO₃ solution (50 mL), dried with sodium sulfate and concentrated to yield 4-propylpiperidine-2,6-dione (V) as a colorless solid. Yield: 3.6 gm (80.4%), Purity by HPLC: 98.9%. M.R: 110-113° C., Example-12: Preparation of 4-propylpiperidine-2,6-dione (II) from Unwanted isomer (R)-3-(2-amino-2-oxoethyl) hexanoic acid (IIa) Using p-toluenesulfonic acid A mixture of Enantiomeric enriched 3-(2-amino-2-oxoethyl) hexanoic acid (IIa) (5.0 gm, 0.029 mol) and para-toluenesulfonic acid (0.55 gm, 0.0029 mol) were suspended in toluene (50 mL) and stirred at 105° C. to 110° C. for 15 hours and liberated water was collected using Dean-Stark apparatus. The reaction mixture was cooled to 25° C. to 30° C. and filtered. The filtrate was washed with 5% NaHCO₃ solution (50 mL), dried with sodium sulfate and concentrated to yield 4-propylpiperidine-2,6-dione (V) as a color less solid. Yield: 3.8 gm (84.8%), Purity by HPLC: 99.8%. M.R: 111-113° C.

Example-13: Preparation of Brivaracetam from (I)

The compound (I) is reacted with (R)-2-bromobutyric acid or its ethyl ester using sodium hydride to obtain Brivaracetam as reported in U.S. Pat. No. 8,338,621 or 8,957,226.

We claim:

1. A process for the preparation of brivaracetam having the structure:

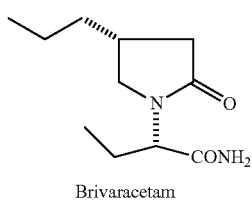

Brivaracetam comprising:
a) reacting (S)-3-(2-amino-2-oxoethyl) hexanoic acid having the structure (II):

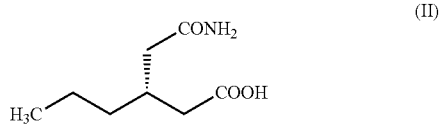

with a chlorinating agent selected from the group consisting of trichloroisocyanuric acid, sodium dichloroisocyanurate and N-chlorosuccinimide, in a solvent selected from the group consisting of methanol, ethanol, acetonitrile, and dimethylformamide at a temperature between 20° C. and 40° C. to produce (S)-3-(2-(chloroamino)-2-oxoethyl) hexanoic acid having the structure (III):

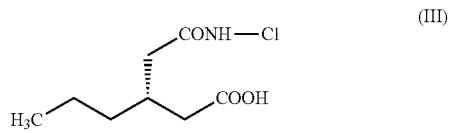

b) reacting (III) with sodium hydroxide in water, initially at a temperature between 15° C. and 30° C., and later at a temperature between 85° C. and 95° C. to produce (R)-4-propyl-pyrrolidin-2-one having the structure (I)

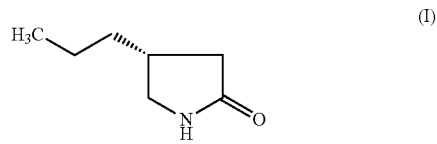

or optionally, the compound (III) is reacted with sodium hydroxide at a temperature between 15° C. and 30° C. to obtain (R)-3-(aminomethyl) hexanoic acid having the structure (IV)

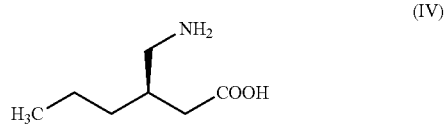

followed by cyclizing the compound (IV) at a temperature between 85° C. and 95° C. to form (R)-4-propyl-pyrrolidin-2-one (I)

c) converting the reaction product of step (b) or (c) into brivaracetam.

2. A compound (S)-3-(2-(chloroamino)-2-oxoethyl) hexanoic acid having the structure (III).

3. The process as claimed in claim 1, wherein the (S)-3-(2-amino-2-oxoethyl) hexanoic acid (II) is prepared by:
a) reacting 4-propyl piperidine-2,6-dione having the structure (V)

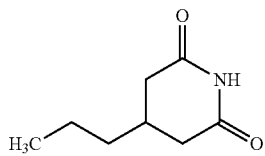

(V)

with an aqueous solution of sodium hydroxide at a temperature between 40° C. and 60° C. to obtain a racemic mixture of 3-(2-amino-2-oxoethyl) hexanoic acid having the structure (VI):

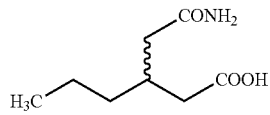

VI b) reacting racemic (VI) with (S)-(−)-1-Phenylethylamine in chloroform containing 2 to 5% ethanol at a temperature between 40° C. and 55° C. followed by cooling to obtain (S)-3-(2-amino-2-oxoethyl) hexanoic acid (II) as a salt of (S)-(−)-1-Phenylethylamine; and c) hydrolyzing the precipitated salt to obtain (S)-3-(2-amino-2-oxoethyl) hexanoic acid (II).

4. A process as claimed in claim 3, wherein the isomer, (R)-3-(2-amino-2-oxoethyl) hexanoic acid having the structure (IIa), remaining after obtaining (S)-3-(2-amino-2-oxoethyl) hexanoic acid (II) from the racemic mixture as per the reaction of stage (b),

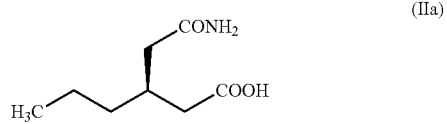

(IIa)

is heated in toluene in the presence of a catalyst selected from the group consisting of boron trioxide, para-toluenesulfonic acid and sulfuric acid at a temperature between 100° C. and 110° C. to obtain 4-propyl piperidine-2,6-dione (V).

* * * * *